United States Patent
Kashiwabara et al.

(10) Patent No.: US 6,200,588 B1
(45) Date of Patent: Mar. 13, 2001

(54) BLOOD-COMPATIBLE COMPOSITION AND MEDICAL DEVICE USING SAME

(75) Inventors: Susumu Kashiwabara; Hidenori Tanaka; Masayoshi Satoh, all of Ohtsu (JP)

(73) Assignee: Toyo Boseki Kabushiki Kaisha, Osaka (JP)

(*) Notice: Subject to any disclaimer, the term of this patent is extended or adjusted under 35 U.S.C. 154(b) by 0 days.

(21) Appl. No.: 09/324,569

(22) Filed: Jun. 2, 1999

(51) Int. Cl.$^7$ .............................. A61F 2/00; B05D 3/00; A01N 43/04; A01N 33/12
(52) U.S. Cl. .................... 424/423; 427/2.1; 427/2.24; 427/2.3; 514/56; 514/642; 514/822
(58) Field of Search ..................... 427/2.1, 2.24, 427/2.25, 2.3; 514/1, 23, 54, 56, 642, 822

(56) References Cited

U.S. PATENT DOCUMENTS 3,717,502  2/1973  Masuhara et al. .

FOREIGN PATENT DOCUMENTS

| 0 219 053 | 4/1987 | (EP) . |
|---|---|---|
| 0 769 503 | 4/1997 | (EP) . |
| 0769503A2 * | 4/1997 | (EP) . |
| 0 781 566 | 7/1997 | (EP) . |
| 0781566A2 * | 7/1997 | (EP) . |
| WO 92/00747 | 1/1992 | (WO) . |

OTHER PUBLICATIONS

Patent Abstracts of Japan, vol. 1998, No. 11 (Sep. 30, 1998) (JP 10 152579 A (Jun. 9, 1998)).
Patent Abstracts of Japan, vol. 1998, No. 11 (Sep. 30, 1998) (JP 10 155898 A (Jun. 16, 1998)).
Database WPI, Section Ch, Week 199307, Derwent Publications Ltd., London, GB Class A96, AN 1993–054822 (XP002121868) (JP 05 003916 A (Jan. 14, 1993)).
Database WPI, Section Ch, Week 199904, Derwent Publications Ltd., London,GB Class A11, AN 199–038645 (XP002121869) (JP 10 295800 A (Nov. 10 1998)).
Database WPI, Section Ch, Week 199935, derwent Publications Ltd., London, GB Class B04, AN 199–411994 (XP002121870) (JP 11 164882 A (Jun. 22, 1999)).

\* cited by examiner

*Primary Examiner*—Jose' G. Dees
*Assistant Examiner*—Marina Lamm
(74) *Attorney, Agent, or Firm*—Leydig, Voit & Mayer, Ltd

(57) ABSTRACT

The present invention provides a blood-compatible composition containing an ionic complex consisting of an organic cationic compound and heparin or a derivative thereof, wherein the organic cationic compound is an ammonium or a phosphonium bound with four aliphatic alkyl groups, the four aliphatic alkyl groups having a total number of carbon atoms of 24 to 32, and has at least 2 alkyl groups having not less than 10 carbon atoms. A medical device capable of long-term sustention of antithrombogenicity can be produced by coating the surface of the medical device with the composition.

7 Claims, No Drawings

BLOOD-COMPATIBLE COMPOSITION AND MEDICAL DEVICE USING SAME

TECHICAL FIELD OF THE INVENTION

The present invention relates to a blood-compatible composition useful as a coating material for medical devices used in contact with blood. The present invention also relates to a medical device coated with said composition, and having an improved compatibility with blood.

BACKGROUND OF THE INVENTION

Along with the progress of medicine, more medical devices made from a polymer material have been widely used, and highly advanced medical devices such as assistant circulation devices (e.g., artificial heart, artificial kidney, pump-oxygenator, intra-aortic balloon pumping and the like), catheters for various diagnoses and therapies, synthetic vascular prosthesis and the like have been put to practical use. However, most of these medical devices are made from polymer materials developed for industrial use without modification, and they require a combined use of an anticoagulant when in use, that prevents coagulation of blood on contact with the medical devices.

However, anticoagulants not only prevent coagulation on the surface of a medical device but also deprive systemic hemostatic function. The use, therefore, is associated with the risk of causing complications such as hemorrhage at the site of insertion or use of medical device, at an operative wound and, in a serious case, from a cerebral vessel. Thus, in an attempt to prevent the above-mentioned complications, methods have been studied that involve imparting antithrombogenicity to a medical device, thereby to reduce administration of anticoaglant.

As a method for imparting antithrombogenicity to a medical device, there have been practiced (A) a method comprising mixing highly fine particles of a polymer material and an anticoagulant substance (e.g., heparin), dispersing the mixture in a solvent and applying the resulting dispersion onto a medical device, (B) a method comprising introducing cation groups such as quaternary ammonium salts into a polymer, dissolving the cation group-containing polymer in a solvent, applying the solution onto a medical device and bringing an aqueous solution of heparin into contact therewith to form ionic bonds between anion groups in heparin and cation groups in the polymer, (C) a method comprising introducing amino groups or aldehyde groups into heparin, directly immobilizing substances or functional groups capable of crosslinking with the above-mentioned functional groups onto a medical device to be a substrate and covalently binding them to immobilize heparin, and (D) a method comprising binding organic cations to anion groups in heparin to make the heparin water-insoluble but soluble to a specific organic solvent and applying the heparin solution onto the medical device.

According to the method (A), however, heparin is directly eluted into blood, so that quick elution occurs in the early stage and antithrombogenic effect is soon disappears. In addition, small holes remain on the surface of the medical device after elution of heparin, thereby possibly causing formation of thrombus on the holes.

The method (B) can provide an antithrombogenic material capable of maintaining higher anticoagulant activity for a long time due to ionic bond. However, this method requires two separate steps of coating a medical device with a quaternary ammonium salt-containing polymer to be a substrate and of binding heparin to the surface of the coated medical device. This in turn increases production cost of a medical device to be in contact with blood, which should be disposable.

The method (C) aims at antithrombogenicity retained for an extended period of time by semi-permanently immobilizing heparin on the surface of a medical device. However, the heparin immobilized on the surface by a covalent bond has limited mobility and cannot bind sufficiently with antithrombin III required for an expression of antithrombogenicity, to the point that the surface cannot exert sufficient antithrombogenicity.

The method (D) comprises dissolving water-insoluble toridecylmethylammonium chloride in isopropyl alcohol, applying the solution onto the surface of a medical device, and then bringing the surface into contact with an aqueous solution of heparin to form an ionic complex of toridecylmethylammonium and heparin on the surface, whereby to provide antithrombogenicity. Like the method of (B), this method again requires two separate steps of coating a medical device with toridecylmethylammonium chloride and of binding heparin, which is undesirable from the aspects of cost and work efficiency.

For this shortcoming to be obliterated, a method has been proposed, which comprises dissolving an ionic complex of a benzalkonium salt and heparin in isopropyl alcohol and applying the solution onto the surface of a medical device. According to this method, the ionic complex is formed first, so that a single step of coating is sufficient. In addition, this solution is sold on the market and easily available. However, benzalkonium salts are produced from an aromatic halide as a staring material, which leaves an issue with the safety of residual starting material. Furthermore, the high cytotoxicity of the resultant benzalkonium salt, as evidenced by the use thereof as a bacteriocide during operation, poses the risk of hemolysis once it elutes out into the blood. Another problem of this method is in connection with the retention of antithiombogenicity during a long-term use of the medical device, because this ionic complex has poor durability in blood.

As can be appreciated from the foregoing, known methods have, without exception, problems in at least one aspect from long-term durability of antithrombogenic effect, production efficiency, production cost and safety.

It is therefore an object of the present invention to provide a means for producing a medical device capable of retaining stable antithrombogenicity for an extended period of time, easily and economically.

SUMMARY OF THE INVENTION

The present invention is based on the finding that an ionic complex comprising an organic cationic compound having a specific number of total carbon atoms, and heparin or a heparin derivative is a useful coating material capable of imparting a sustained antithiombogenicity to a medical device.

Accordingly, the present invention provides a novel blood-compatible composition comprising an ionic complex comprising an organic cationic compound, and heparin or a derivative thereof, the organic cationic compound being an ammonium or a phosphonium bound with 4 aliphatic alkyl groups, and the 4 aliphatic alkyl groups having a total number of carbon atoms of 24 to 32 and at least 2 of the alkyl groups having not less than 10 carbon atoms; preferably, the blood-compatible composition, wherein at least two alkyl groups are methyl; and more preferably, the blood-compatible composition, wherein the alkyl groups having 10 or more carbon atoms have the same number of carbon atoms. The present invention also provides a blood-compatible composition comprising two or more kinds of the above-mentioned ionic complexes.

The present invention further provides a medical device whose surface is coated with any of the above-mentioned ionic complexes.

The composition of the present invention, which comprises the above-noted particular organic cationic compound, and heparin or a derivative thereof, shows superior antithrombogenic effect as compared to known coating materials for medical devices. The inventive composition shows stable retention of the effect for a long time. Therefore, it is particularly useful as a coating material for a medical device potent in contact with blood when in use. Furthermore, the inventive composition allows for the production of an antithrombogenic medical device by a single application of the coating, which is extremely useful in terms of cost and work efficiency.

DETAILED DESCRIPTION OF THE INVENTION

The present invention is characterized by the relationship present in an ionic complex of heparin and an organic cation group in the method of (D) above between the total number of carbon atoms in 4 alkyl groups binding to the nitrogen atom or phosphorus atom, and the anticoagulant activity of heparin in the ionic complex, wherein an ammonium or phosphonium bound with 4 aliphatic alkyl groups is used as the organic cation group.

In the composition of the present invention, the total number of carbon atoms of alkyl groups in the organic cationic compound is 24 to 32, preferably 25 to 31, and more preferably 26 to 30. When the total number of carbon atoms of alkyl groups is less than 24, heparin is rapidly eluted into blood and the antithrombogenicity cannot be sustained for a long time. On the other hand, when the total number of carbon atoms is more than 32, heparin in the ionic complex cannot exert sufficient activity at the contact site with blood due to high hydrophobicity of the alkyl groups.

Furthermore, at least 2 of the alkyl groups in the organic cationic compound are long-chain aliphatic alkyl groups having 10 or more carbon atoms, preferably 12 to 14 carbon atoms, so that the compound can prevent the elution of heparin while maintaining sufficient activity of heparin on the surface of a medical device. These long-chain aliphatic alkyl groups may have the same or different carbon numbers, but they preferably have the same carbon numbers for facilitated synthesis and the quality control.

In a preferable embodiment of the present invention, two of the alkyl groups in the organic cationic compound are long-chain aliphatic alkyl groups as mentioned above, and the other two alkyl groups are lower alkyl groups having 1 to 4 carbon atoms. Particularly, the lower alkyl groups are preferably methyl. Such lower alkyl group is advantageous for binding with heparin because of less steric hindrance.

The blood-compatible composition of the present invention comprises an ionic complex of an organic cationic compound and heparin or a heparin derivative, as an essential component. As used herein, the heparin derivative may be any derivative of heparin as long as it retains an anticoagulant activity, and may be, for example, sodium heparin, potassium heparin, calcium heparin, low molecule heparin, heparamin, epoxidated heparin and the like.

The blood-compatible composition of the present invention can comprise one kind of the above-mentioned ionic complex or two or more kinds of the above-mentioned ionic complexes.

In addition, the blood-compatible composition of the present invention can further comprise an ionic complex of a cationic compound not encompassed in the present invention and heparin or a heparin derivative, as long as it comprises at least one ionic complex containing an organic cationic compound having the above-noted characteristics. Such a cationic compound preferably includes an organic cationic compound having 4 alkyl groups wherein the total number of carbon atoms in the alkyl groups is less than 24 or more than 32, because it can optionally control the amount of heparin to be eluted.

Alternatively, the inventive ionic complex can be mixed with other polymers and applied to the surface of a medical device. Such polymers include, for example, polyurethane, poly(vinyl chloride), polycarbonate and the like.

The blood-compatible composition of the present invention can be produced by any method, for example, by the following method.

First, heparin or a heparin derivative is dissolved in an appropriate amount of water to give an aqueous solution. Separately, an ammonium salt or a phosphonium salt having 4 alkyl groups, wherein the total number of carbon atoms in the alkyl groups is 24 to 32, is dissolved in $C_1$–$C_3$ alcohol. Then, $C_1$–$C_3$ alcohol is added to the aqueous solution of heparin, and water is added to the solution of the ammonium salt or phosphonium salt, respectively, such that both solvents have the same final composition. When heparin or ammonium salt or phosphonium salt precipitates in this step, the solution is heated at least to the temperature at which the precipitate dissolves to give a completely homogenous solution.

Subsequently, the solution of ammonium salt or phosphonium salt is added dropwise to the heparin solution under stirring. Heparin and the organic cation group react almost instantaneously to generate a precipitate. This precipitate is recovered and thoroughly washed to remove unreacted organic cation and heparin.

The resulting precipitate is centrifuged and lyophilized to remove the solvent completely, and dissolved in an organic solvent for coating. The organic solvent varies depending on the object to be coated, namely, the medical device to be coated. For example, THF is preferably used for poly(vinyl chloride) (hereinafter referred to as PVC) which is frequently utilized as a material for medical devices, and alicyclic hydrocarbon or aliphatic hydrocarbon is preferably used for polycarbonate. When the resultant ionic complex is insoluble in these organic solvents, the solubility parameters can be controlled by adding a polar solvent in the case of a non-polar solvent or a non-polar solvent in the case of a polar solvent to the organic solvent, whereby the ionic complex in the organic solvent can be dissolved.

As used herein, a medical device refers to any medical device that comes into contact with blood when in use. Such a medical device includes, for example, assistant circulation devices (e.g., artificial heart, artificial kidney, pump-oxygenator, intra-aortic balloon pumping and the like), catheters for various diagnoses and therapies, synthetic vascular prosthesis and the like.

The present invention is explained in more detail in the following by way of Examples. They are mere examples and do not limit the scope of the present invention in any way.

EXAMPLE 1

Dimethyldidodecylphosphonium chloride (18 parts) and dimethylditetradecylphosphonium chloride (60 parts) were added to methanol (50 parts) under stirring and dissolved.

After confirming they were completely dissolved, water was added to the concentration of 70%. Then, heparin (32 parts) was dissolved in water (70 parts), and methanol was added to the concentration of 30%, during which, a part of heparin precipitated out to form a suspension. This suspension was heated to 70° C. to make same a homogenous solution. The solution of phosphonium salt was dropwise added to the solution of heparin under stirring. The reactant was insoluble in the solvent, and immediately precipitated. This precipitate was recovered and washed thoroughly to remove the unreacted heparin and phosphonium salt. The precipitate was centrifuged to remove water and finally lyophilized to give a white powder. The resulting white powder was dissolved in THF to the concentration of 0.1%. A PVC tube (3 mm in inner diameter) was coated with the solution. One end of the tube was clamped to give a test tube-like tube (5 cm in length). Similarly, a tube (3 mm in inner diameter, 1 m in length) was coated with this solution, one end of which was connected to a three-way cock.

EXAMPLE 2

The white powder obtained in Example 1 was dissolved in THF to the concentration of 0.1%. To this solution was added polyether type segmented polyurethane (Tecoflex hardness 80A, Thermedics Inc.) which was dissolved to the concentration of 0.1%. A PVC tube (3 mm in inner diameter) was coated with the solution, and one end of the tube was clamped to give a test tube-like tube (5 cm in length). Similarly, a tube (3 mm in inner diameter, 1 m in length) was coated with this solution, one end of which was connected to a three-way cock.

EXAMPLE 3

Dimethyldidodeceylammonium chloride (6 parts) and dimethylditetradecylammonium chloride (19 parts) were added to methanol (25 parts) under stirring and dissolved. After confirming they were completely dissolved, water was added to the concentration of 70%, during which a part of ammonium salt precipitated out. The suspension was heated to 50° C. to make same a homogeneous solution. Then, heparin (10 parts) was dissolved in water (25 parts), and methanol was added to the concentration of 30%. In this step, a part of heparin also precipitated to form a suspension. This suspension was heated to 70° C. to make same a homogenous solution. The solution of ammonium salt was dropwise added to the solution of heparin under stirring. The reactant was insoluble in the solvent, and immediately precipitated. This precipitate was recovered and washed thoroughly to remove unreacted heparin and ammonium salt. Further, the precipitate was centrifuged to remove water and finally lyophilized to give a white powder. The resulting white powder was dissolved in THF to the concentration of 0.1%. A PVC tube (3 mm in inner diameter) was coated with the solution, and one end of the tube was clamped to give a test tube-like tube (5 cm in length). Similarly, a tube (3 mm in inner diameter, 1 m in length) was coated with this solution, one end of which was connected to a three-way cock.

EXAMPLE 4

Dimethyldidodecylammonium chloride (17 parts), dimethylditetradecylammonium chloride (58 parts), dimethyldipalmitylammonium chloride (29 parts) and dimethyldistearylammonium chloride (31 parts) were added to methanol (50 parts) under stirring and dissolved. After confirming they were completely dissolved, water was added to the concentration of 70%, during which a part of ammonium salt precipitated but dissolved by heating the suspension to 70° C. to give a homogenous solution. Then, heparin (50 parts) was dissolved in water (120 parts), and methanol was added to the concentration of 30%. In this step, a part of heparin also precipitated to form a suspension, but the suspension was heated to 70° C. to make same a homogenous solution. The solution of ammonium salt was dropwise added to the solution of heparin under stirring. The precipitate was insoluble in the solvent, and immediately precipitated. This precipitate was recovered and washed thoroughly to remove unreacted heparin and ammonium salt. Further, the precipitate was centrifuged to remove water and finally lyophilized to give a white powder. The resulting white powder was dissolved in THF to the concentration of 0.1%. A PVC tube (3 mm in inner diameter) was coated with the solution, and one end of the tube was clamped to give a test tube-like tube (5 cm in length). Similarly, a tube (3 mm in inner diameter, 1 m in length) was coated with this solution, one end of which was connected to a three-way cock.

EXAMPLE 5

Dibutyldilaurylphosphonium chloride (27 parts) was added to methanol (15 parts) under stirring and dissolved. After confirming they were completely dissolved, water was added to the concentration of 70% and the solution was heated to 50° C. Then, heparin (10 parts) was dissolved in water (25 parts), and methanol was added to the concentration of 30%. In this step, a part of heparin precipitated but dissolved by heating the suspension to 70° C. to give a homogenous solution. The solution of phosphonium salt was dropwise added to the solution of heparin under stirring. The reactant was insoluble in the solvent, and immediately precipitated. This precipitate was recovered and washed thoroughly to remove unreacted heparin and phosphonium salt. Further, the precipitate was centrifuged to remove water and finally lyophilized to give a white powder. The resulting white powder was dissolved in THF to the concentration of 0.1%. A PVC tube (3 mm in inner diameter) was coated with the solution, and one end of the tube was clamped to give a test tube-like tube (5 cm in length). Similarly, a tube (3 mm in inner diameter, 1 m in length) was coated with this solution, one end of which was connected to a three-way cock.

COMPARATIVE EXAMPLE 1

Dimethyldidecylammonium chloride was added to methanol (19.5 parts) under stirring and dissolved. After confirming it was completely dissolved, water was added to the concentration of 70% and the solution was heated to 70° C. to give a homogenous solution. Then, heparin (10 parts) was dissolved in water (25 parts), and methanol was added to the concentration of 30%. In this step, a part of heparin precipitated to form a suspension. This suspension was heated to 70° C. to make same a homogenous solution. The solution of ammonium salt was dropwise added to the solution of heparin under stirring. The reactant was insoluble in the solvent, and immediately precipitated. This precipitate was recovered and washed thoroughly to remove unreacted heparin and ammonium salt. Further, the precipitate was centrifuged to remove water and finally lyophilized to give a white powder. The resulting white powder was dissolved in THF to the concentration of 0.1%. A PVC tube (3 mm in inner diameter) was coated with the solution, and one end of the tube was clamped to give a test tube-like tube (5 cm in length). Similarly, a tube (3 mm in inner diameter, 1 m in length) was coated with this solution, one end of which was connected to a three-way cock.

COMPARATIVE EXAMPLE 2

Benzylmethylstearylammonium chloride (65 parts) was added to methanol (25 parts) under stirring and dissolved. After confirming it was completely dissolved, water was added to the concentration of 70%. Then, heparin (30 parts) was dissolved in water (70 parts), and methanol was added to the concentration of 30%. In this step, a part of heparin precipitated to form a suspension, but this suspension was heated to 70° C. to make same a homogenous solution. The solution of ammonium salt was dropwise added to the solution of heparin under stirring. The precipitate was insoluble in the solvent, and immediately precipitated. This precipitate was recovered and washed thoroughly to remove unreacted heparin and ammonium salt. Further, the precipitate was centrifuged to remove water and finally lyophilized to give a white powder. The resulting white powder was dissolved in THF to the concentration of 0.1%. A PVC tube (3 mm in inner diameter) was coated with the solution, and one end of the tube was clamped to give a test tube-like tube (5 cm in length). Similarly, a tube (3 mm in inner diameter, 1 m in length) was coated with this solution, one end of which was connected to a three-way cock.

COMPARATIVE EXAMPLE 3

Tridodecylmethylammonium chloride (10 parts) was dissolved in isopropyl alcohol to the concentration of 1%. A PVC tube (3 mm in inner diameter) was coated with the solution, and an aqueous solution of 1% heparin was filled therein to immobilize heparin. One end of the tube was clamped to give a test tube-like tube (5 cm in length). Similarly, a tube (3 mm in inner diameter, 1 m in length) was coated with the above solution of tridodecylmethylammonium chloride, and an aqueous solution of 1% heparin was filled therein to immobilize heparin. One end of this tube was connected to a three-way cock.

TEST EXAMPLE 1

Each test tube-like tube prepared in Examples 1–5 and Comparative Examples 1–3 was filled with bovine blood supplemented with citric acid (1.5 ml) and incubated at 37° C. To the tube was added 1/40 N calcium chloride solution to start coagulation. After incubation for 3 min, an aqueous solution of trisodium citrate was added again to stop the coagulation. The thrombus coagulated in the tube was harvested and accurately weighed. For observation of the durability of blood-compatibility, the same evaluation was performed after the tube was immersed in physiological saline for a week. In each experiment, the same measurement was conducted using a non-coated PVC tube as a control. The results are shown in Table 1. The values in Table 1 represent relative weights of thrombus generated in the tubes, wherein the amount of thrombus generated in a glass test tube having the same diameter was taken as 1.

TABLE 1

|  | Example | | | | | Comparative Example | | | |
| --- | --- | --- | --- | --- | --- | --- | --- | --- | --- |
| Treatment | 1 | 2 | 3 | 4 | 5 | 1 | 2 | 3 | Non-coated |
| Not treated | 0 | 0 | 0 | 0 | 0 | 12 | 32 | 11 | 78 |
| Immersed in saline for 1 week | 0 | 2 | 4 | 0 | 0 | 78 | 65 | 67 | 85 |

TEST EXAMPLE 2

From one opening of the three-way cock connected with each tube prepared in Examples 1–5 and Comparative Examples 1–3, fresh blood obtained from a rabbit (Japanese white) supplemented with citric acid was infused into the tube. Simultaneously, 1/40 N calcium chloride solution was infused thereinto from the other opening of the cock. The blood and calcium chloride solution were infused with syringe pumps by 50 ml/min and 5 ml/min, respectively. The blood was re-activated in the tube and began to coagulate. After complete passage of the blood through the tube, the location of thrombus was observed and the area thereof was measured. The measurement of the area was based on the observation of the adhesion of fibrin nectar onto the surface of the tube with a scanning electron microscope. Further, the same evaluation was performed after circulation of physiological saline heated at 37° C. in the tube for a week. In each experiment, the same measurement was carried out using a non-coated PVC tube as a control. The results are shown in Table 2. The values in Table 2 represent percentages of the areas to which the thrombus adhered after the circulation of the blood.

TABLE 2

|  | Example | | | | | Comparative Example | | | |
| --- | --- | --- | --- | --- | --- | --- | --- | --- | --- |
| Treatment | 1 | 2 | 3 | 4 | 5 | 1 | 2 | 3 | Non-coated |
| Not treated | 0 | 0 | 0 | 0 | 0 | 0 | 0 | 26 | 88 |
| Immersed in saline for 1 week | 0 | 0 | 0 | 0 | 0 | 36 | 54 | 76 | 85 |

As is obvious from Table 1 and Table 2, the PVC tubes coated with the ionic complexes, which consisted of the organic cationic compound of the present invention and heparin, showed higher and long-term sustention of anti-thrombogenicity as compared to those coated with the ionic complexes of the cation groups falling outside the scope of the present invention and heparin.

What is claimed is:

1. A blood-compatible composition comprising an ionic complex comprising at least two organic cationic compounds and heparin or a heparin derivative, wherein said at least two organic cationic compounds comprise at least the following two compounds (a) and (b):

(a) a compound selected from a group consisting of an ammonium compound and a phosphonium compound, both having four aliphatic alkyl groups, wherein two of the four aliphatic alkyl groups are methyl and the other two are long chain aliphatic alkyl groups having 12 carbon atoms, and (b) a compound selected from the group consisting of an ammonium compound and a phosphonium compound, both having four aliphatic alkyl groups, wherein said compounds have at least two alkyl groups having not less than 10 carbon atoms each and wherein the four aliphatic alkyl groups have 30 to 38 carbon atoms in total.

2. The blood compatible composition of claim 1, wherein two of the four aliphatic alkyl groups of the compound (b) are methyl and the other two are long chain aliphatic alkyl groups having 14 carbon atoms.

3. The blood compatible composition of claim 1, wherein two of the four aliphatic alkyl groups of the compound (b) are methyl and the other two are long chain aliphatic alkyl groups having 16 carbon atoms.

4. The blood compatible composition of claim 1, wherein two of the four aliphatic alkyl groups of the compound (b)

are methyl and the other two are long chain aliphatic alkyl groups having 18 carbon atoms.

5. The blood compatible composition of claim 1, wherein the compound (b) is at least one compound selected from the group consisting of dimethylditetradecylammonium, dimethylditetradecylphosphonium, dimethyldipalmitylammonium and dimethyldistearylammonium.

6. The blood compatible composition of claim 1, wherein the compound (b) is contained in the amount of 3–7 parts per part of the compound (a).

7. A medical device comprising a surface that is coated with the blood compatible composition of claim 1.

* * * * *

UNITED STATES PATENT AND TRADEMARK OFFICE
CERTIFICATE OF CORRECTION

PATENT NO. : 6,200,588 B1
DATED : March 13, 2001
INVENTOR(S) : Kashiwabara et al.

It is certified that error appears in the above-identified patent and that said Letters Patent is hereby corrected as shown below:

Title page,
Line 11, "London,GB" should read as -- London, GB --.
Line 11, "199-038645" should read as -- 1999-038645 --.
Line 13, "derwent" should read as -- Derwent --.
Line 14, "199-411994" should read as -- 1999-411994 --.

Signed and Sealed this

Twenty-second Day of January, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

| | |
|---|---|
| PATENT NO. | : 6,200,588 B1 |
| APPLICATION NO. | : 09/324569 |
| DATED | : March 13, 2001 |
| INVENTOR(S) | : Kashiwabara et al. |

It is certified that error appears in the above-identified patent and that said Letters Patent is hereby corrected as shown below:

Title Page

Item (75): INVENTORS: "Masayoshi Satoh" should read as --Masaki Sato--.

Signed and Sealed this

First Day of May, 2007

JON W. DUDAS
*Director of the United States Patent and Trademark Office*